(12) United States Patent
Bydon et al.

(10) Patent No.: US 10,835,384 B2
(45) Date of Patent: Nov. 17, 2020

(54) FACET JOINT REPLACEMENT DEVICES

(71) Applicant: Mayo Foundation for Medical Education and Research, Rochester, MN (US)

(72) Inventors: Mohamad Bydon, Rochester, MN (US); Chunfeng Zhao, Rochester, MN (US); Panagiotis Kerezoudis, Rochester, MN (US); Brandon A. McCutcheon, Rochester, MN (US); Hugo Giambini, Rochester, MN (US); Timothy L. Rossman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 87 days.

(21) Appl. No.: 15/698,357

(22) Filed: Sep. 7, 2017

(65) Prior Publication Data

US 2018/0071106 A1 Mar. 15, 2018

Related U.S. Application Data

(60) Provisional application No. 62/393,776, filed on Sep. 13, 2016.

(51) Int. Cl.
*A61B 17/70* (2006.01)
*A61F 2/44* (2006.01)
*A61F 2/30* (2006.01)

(52) U.S. Cl.
CPC ........ *A61F 2/4405* (2013.01); *A61B 17/7023* (2013.01); *A61B 17/7025* (2013.01); *A61B 17/7031* (2013.01); *A61B 17/7064* (2013.01); *A61F 2002/30563* (2013.01); *A61F 2002/30565* (2013.01); *A61F 2002/30578* (2013.01); *A61F 2310/00017* (2013.01);
(Continued)

(58) Field of Classification Search
CPC ............ A61B 17/7026; A61B 17/7028; A61B 17/7002–7031; A61B 17/7049–7052; A61B 17/7062; A61B 17/7064; A61F 2/4405
USPC .......................................... 606/247, 257–260
See application file for complete search history.

(56) References Cited

U.S. PATENT DOCUMENTS 5,375,823 A * 12/1994 Navas ................ A61B 17/7005
623/17.15
6,241,730 B1 * 6/2001 Alby .................. A61B 17/7007
403/120
(Continued)

OTHER PUBLICATIONS

Criswell, Amy Jo., "Development of a lumbar facet joint replacement," MS (Master of Science) thesis, University of Iowa, 2013, URL<http://ir.uiowa.edu/etd/2466>, 107 pages.
(Continued)

*Primary Examiner* — Nicholas J Plionis
(74) *Attorney, Agent, or Firm* — Fish & Richardson P.C.

(57) ABSTRACT

Devices and systems can be used to treating spinal conditions. For example, this document describes artificial facet joint systems that can be implanted to treat spinal conditions while facilitating normal stability and motions of the spine. Such systems and methods can be used to treat spinal conditions such as, but not limited to, spondylosis, vertebral fractures, and the like.

18 Claims, 10 Drawing Sheets

(52) U.S. Cl.
CPC ............ *A61F 2310/00023* (2013.01); *A61F 2310/00029* (2013.01); *A61F 2310/00395* (2013.01)

(56) References Cited

U.S. PATENT DOCUMENTS

| | | | | |
|---|---|---|---|---|
| 7,744,633 | B2* | 6/2010 | Berrevoets | A61B 17/7052 606/250 |
| 7,935,134 | B2* | 5/2011 | Reglos | A61B 17/7004 606/254 |
| 8,029,548 | B2* | 10/2011 | Prevost | A61B 17/7031 606/278 |
| 8,202,301 | B2 | 6/2012 | Prevost et al. | |
| 8,287,571 | B2* | 10/2012 | Semler | A61B 17/7031 606/254 |
| 8,353,933 | B2 | 1/2013 | Triplett et al. | |
| 8,709,043 | B2 | 4/2014 | Kwak et al. | |
| 9,050,140 | B2* | 6/2015 | Semler | A61B 17/7004 |
| 9,072,544 | B2* | 7/2015 | Fortin | A61B 17/7023 |
| 2004/0049190 | A1 | 3/2004 | Biedermann et al. | |
| 2005/0113922 | A1* | 5/2005 | Brazenor | A61B 17/70 623/17.11 |
| 2005/0124991 | A1 | 6/2005 | Jahng | |
| 2005/0165396 | A1* | 7/2005 | Fortin | A61B 17/7025 606/257 |
| 2005/0222569 | A1* | 10/2005 | Panjabi | A61B 17/7007 606/257 |
| 2007/0032123 | A1* | 2/2007 | Timm | A61B 17/7007 439/395 |
| 2008/0027436 | A1* | 1/2008 | Cournoyer | A61B 17/7014 606/250 |
| 2008/0033562 | A1 | 2/2008 | Krishna et al. | |
| 2008/0086126 | A1* | 4/2008 | Miller | A61B 17/7014 606/86 R |
| 2008/0091269 | A1* | 4/2008 | Zipnick | A61B 17/1671 623/17.13 |
| 2008/0195208 | A1* | 8/2008 | Castellvi | A61B 17/7023 623/17.15 |
| 2009/0048631 | A1* | 2/2009 | Bhatnagar | A61B 17/7004 606/246 |
| 2009/0099608 | A1* | 4/2009 | Szczesny | A61B 17/7023 606/257 |
| 2010/0069964 | A1* | 3/2010 | Lechmann | A61B 17/7023 606/278 |
| 2010/0211104 | A1* | 8/2010 | Moumene | A61B 17/7028 606/257 |
| 2011/0238119 | A1 | 9/2011 | Moumene et al. | |
| 2013/0338713 | A1* | 12/2013 | Kawakami | A61B 17/888 606/258 |
| 2016/0151093 | A1* | 6/2016 | Barry | A61B 17/705 606/251 |

OTHER PUBLICATIONS

Gornet et al., "Cervical disc arthroplasty with PRESTIGE LP disc versus anterior cervical discectomy and fusion: a prospective, multicenter investigational device exemption study," J. Neurosurg Spine, Nov. 2015, 23(5):558-573.

Lotz et al., "Compression-Induced Degeneration of the Intervertebral Disc: An in Vivo Mouse Model and Finite-Element Study," Spine, Dec. 1998, 23(23):2493-506.

Rajaee et al., "Spinal fusion in the United States," Spine, Jan. 2012, 37(1):67-76.

Rannou et al., "Cyclic tensile stretch modulates proteoglycan production by intervertebral disc annulus fibrosus cells through production of nitrite oxide," Journal of cellular biochemistry, Sep. 2003, 90(1):148-157.

Yoshihara et al., "National trends in the United States, 2000 to 2009," Spine, Feb. 2015, 15(2):265-271.

businesswire.com [BusinessWire] "Research and Markets: US Spinal Surgery Devices Market: Increasing Procedures to Drive Growth," Dec. 14, 2009, Retrieved Mar. 8, 2018, Retrieved online: URL<https://www.businesswire.com/news/home/20091214005893/en/Research-Markets-Spinal-Surgery-Devices-Market-Increasing>, 5 pages.

Gomleksiz et al., "A short history of posterior dynamic stabilization," Advances in Orthopedics, 2012, Article ID 629698, 12 pages.

Nayak et al., "Postero-lateral disc prosthesis combined with a unilateral facet replacement device maintains quantity and quality of motion at a single lumbar level," *International J Spine Surgery.*, 2014, 19 pages.

Serhan et al., "Motion-preserving technologies for degenerative lumbar spine: The past, present, and future horizons," *SAS J.*, 5:75-89, 2011.

YouTube.com [Online Video]. "Alphatec spine—Isobar dynamicrod," Published on Jul. 16, 2014, [Retrieved Mar. 8, 2018] Retrieved from the Internet: URL: https://www.youtube.com/watch?v=1TLbt8zrL1Q, 2 pages.

\* cited by examiner

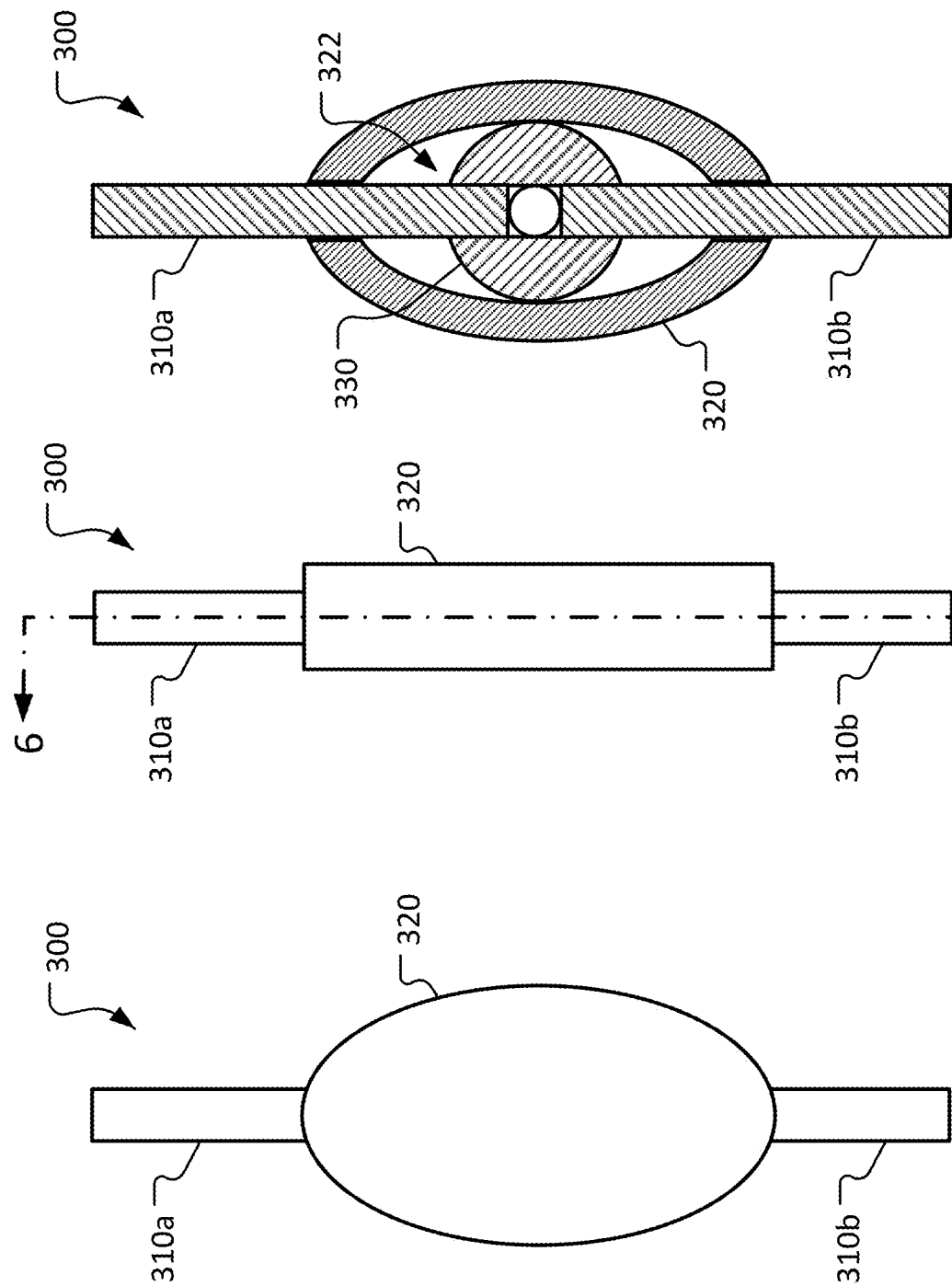

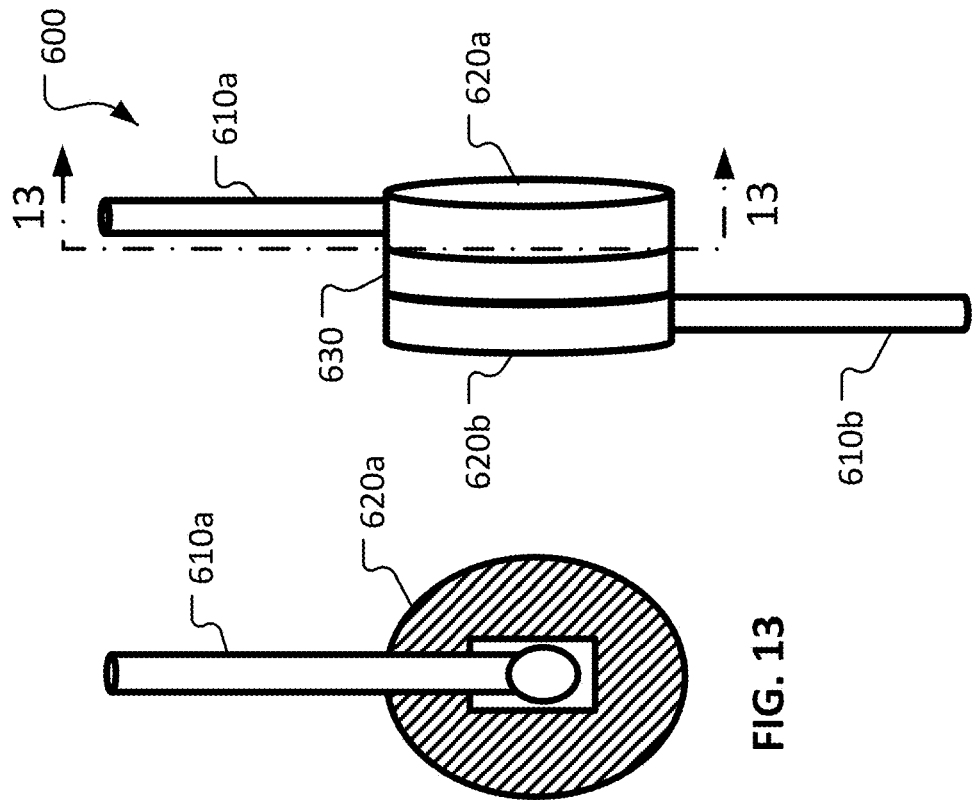
FIG. 14
FIG. 13
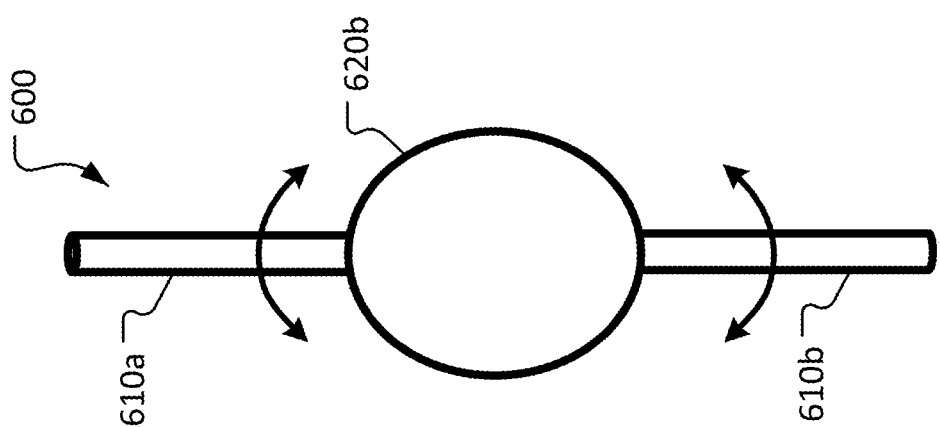
FIG. 12

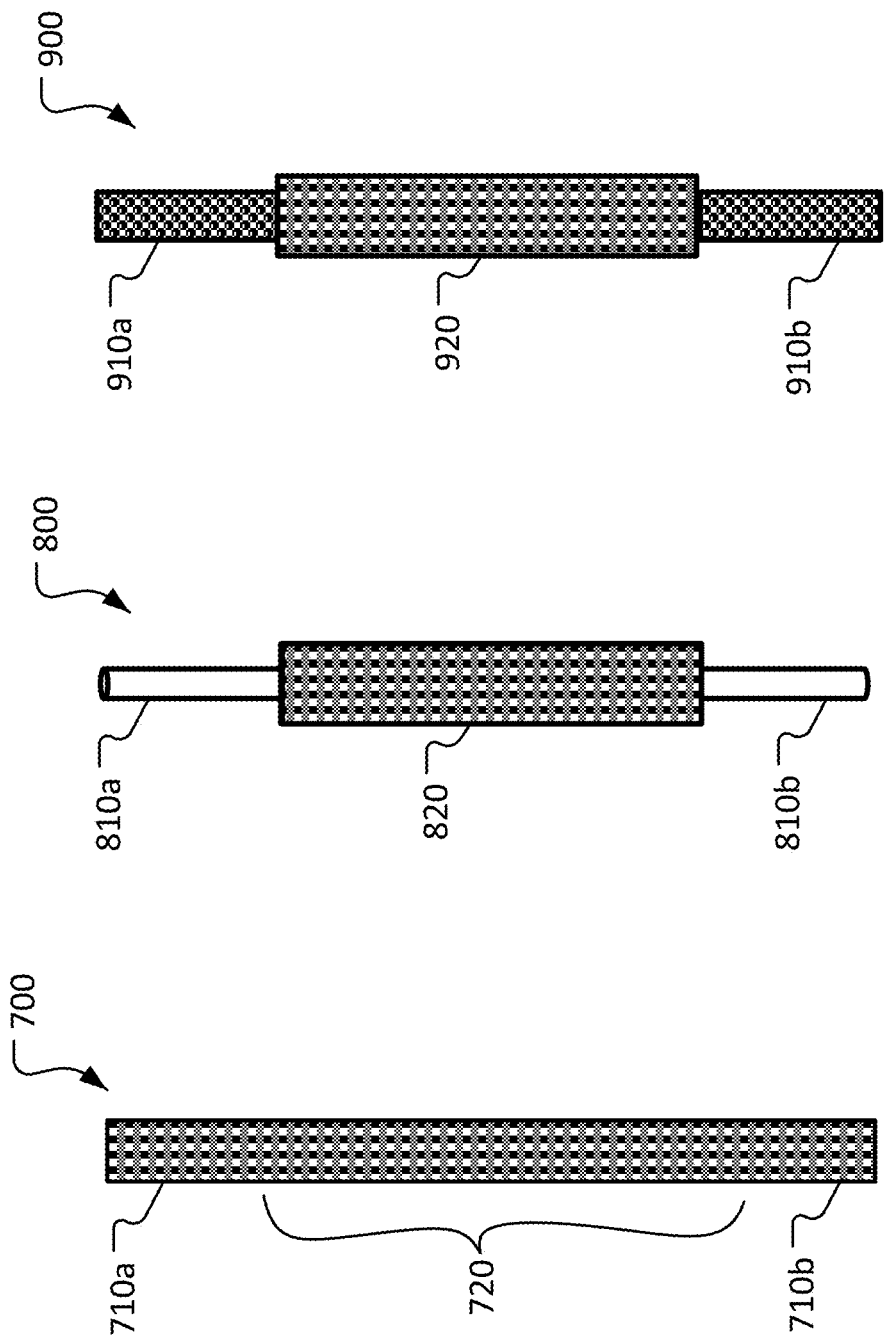

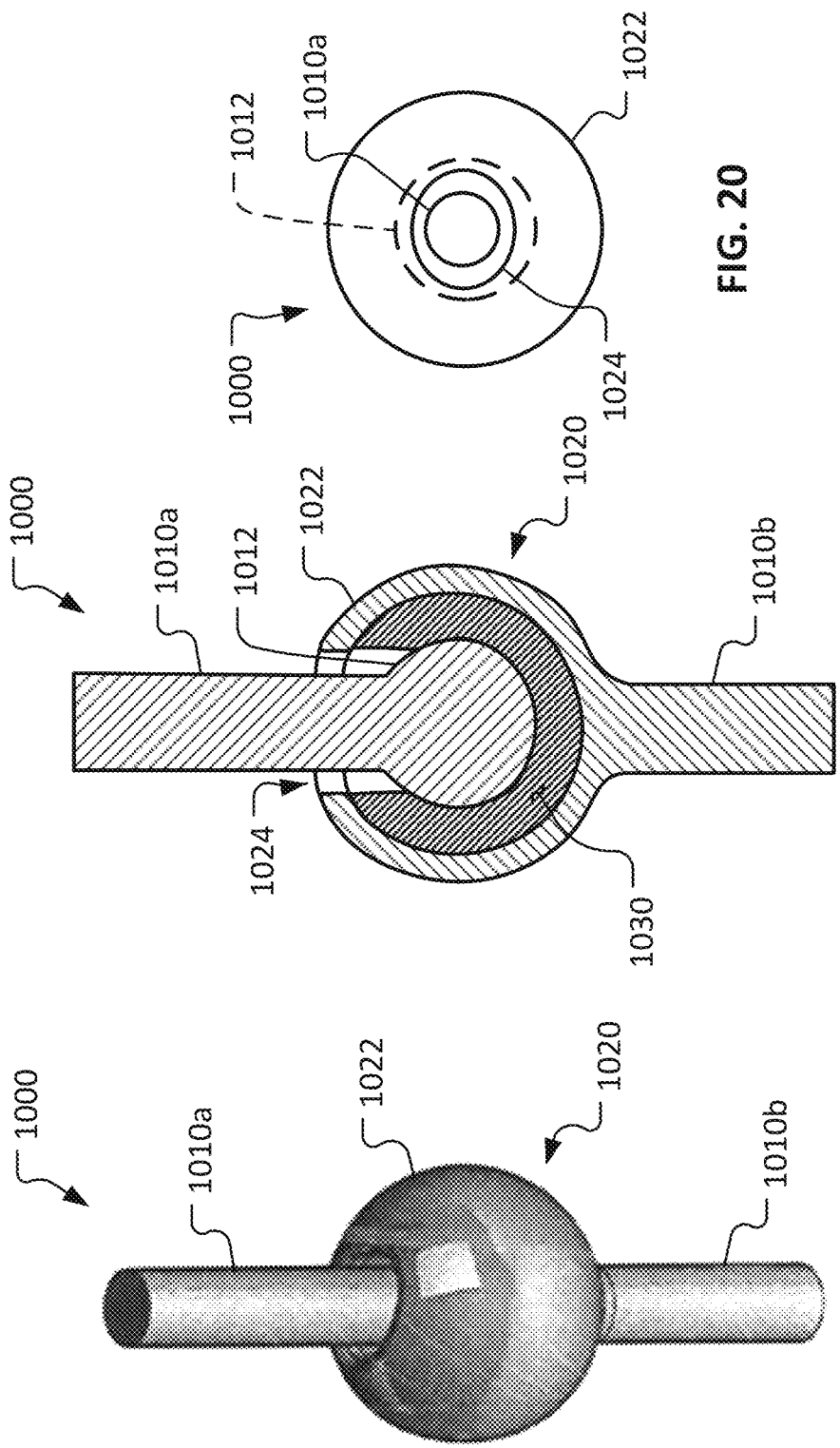

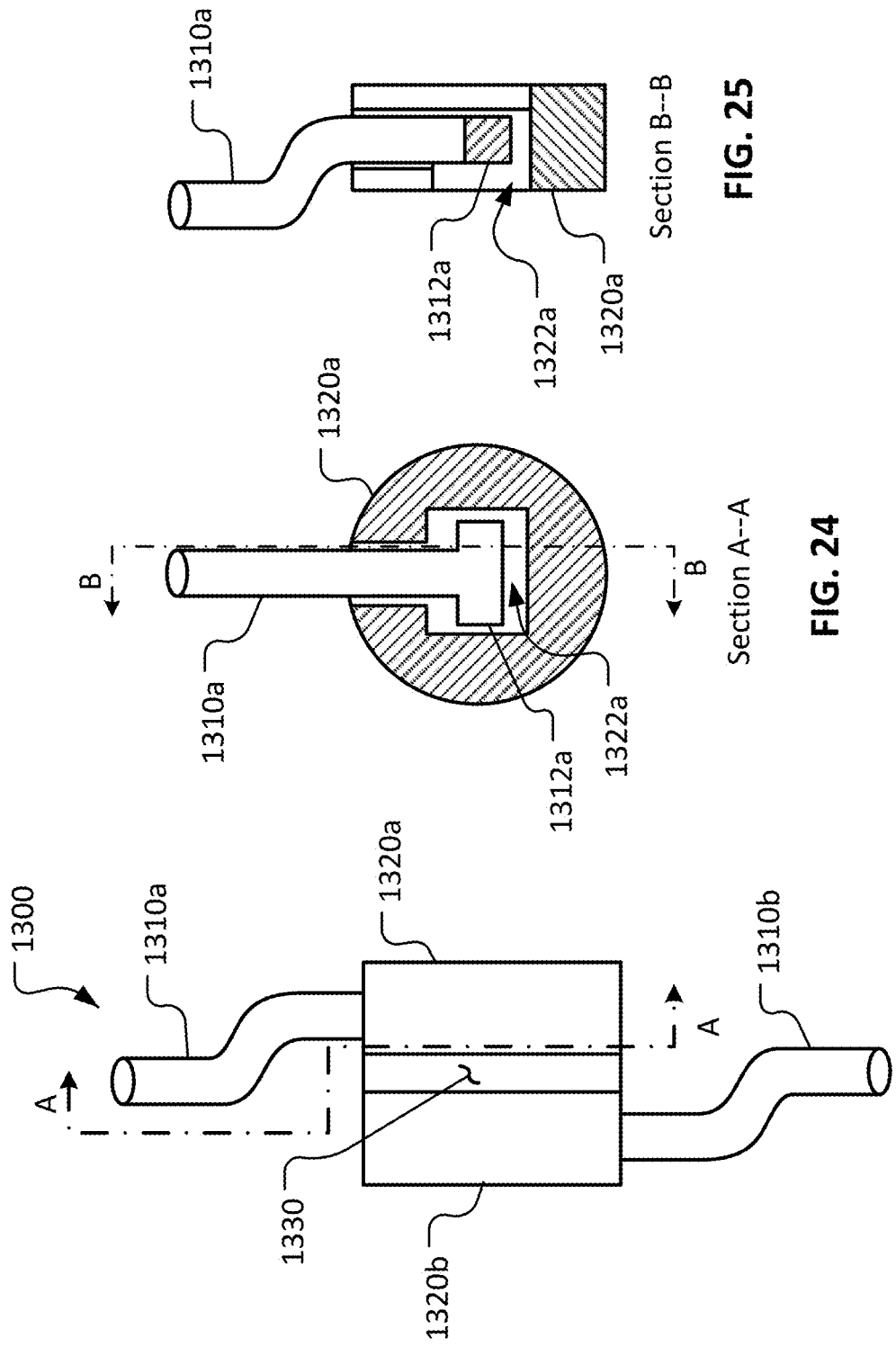

FACET JOINT REPLACEMENT DEVICES

CROSS-REFERENCE TO RELATED APPLICATIONS

This application claims the benefit of U.S. Provisional Application Ser. No. 62/393,776, filed Sep. 13, 2016. The disclosure of the prior application is considered part of (and is incorporated by reference in) the disclosure of this application.

BACKGROUND

1. Technical Field

This document relates to devices and systems for treating spinal conditions. For example, this document relates to artificial facet joint systems that can be implanted to treat spinal conditions while facilitating substantially normal stability and motions of the spine.

2. Background Information

Low back pain (LBP) and neck pain are among the most common patient complaints in the primary care setting. Globally, LBP has been ranked as the greatest contributor to worldwide disability with an estimated annual direct medical cost over $100 billion. According to most recent studies, the mean annual prevalence of LBP is 9-13%, with a lifetime risk up to 65%. Since the mean life expectancy continues to rise in the US population, the number of people with LBP will increase substantially.

The major cause of LBP and neck pain is spondylosis (i.e., degenerative spinal disease); especially amongst the elderly. Though non-operative management strategies can be efficacious, many patients ultimately require surgical treatment of the affected vertebral level. Traditionally, such operations have involved fusion of the spine, which includes placing screws at the vertebrae and a small rod that connects the screws together.

Apart from spondylosis, another widespread application of spinal fusion is for the treatment of vertebral fractures secondary to osteoporosis. Approximately 8 million women and 2 million men suffer from this condition. Another 34 million have low bone mass and are thus at increased risk for osteoporosis. Moreover, an estimated 700,000 of these patients will experience a vertebral compression fracture that will necessitate spinal fusion in order to preserve spinal stability. Current analyses forecast that osteoporosis will continue to increase in prevalence significantly over the next 20 years.

Spinal fusion is an option for the management of spondylosis or fractures secondary to osteoporosis. Spinal fusion has the benefit of allowing for removal of degenerative tissue while simultaneously preserving spinal stability. However, it comes at the cost of reduced range of motion.

SUMMARY

This document provides devices and systems for treating spinal conditions. For example, this document provides artificial facet joint systems that can be implanted to treat spinal conditions while facilitating normal stability and motions of the spine. The systems and methods provided herein can be used to treat spinal conditions such as, but not limited to, spondylosis, spondylolisthesis, cervical or lumbar stenosis, foraminal stenosis, vertebral fractures, and the like.

In one implementation, a facet joint replacement device includes: (i) a housing defining a first opening, a second opening, and an internal space; (ii) a first rod slidingly engaged with the first opening, the first rod including an internal end portion disposed within the internal space and an external end portion disposed outside of the internal space; (iii) a second rod slidingly engaged with the second opening, the second rod including an internal end portion disposed within the internal space and an external end portion disposed outside of the internal space; and (iv) an elastic element disposed within the internal space. The elastic element is coupled to and extending between the internal end portion of the first rod and the internal end portion of the second rod such that the first rod is spaced apart from the second rod by a spacing distance.

Such a facet joint replacement device can optionally include one or more of the following features. The first rod and the second rod may be compressed toward each other such that the elastic element compresses and the spacing distance decreases. The first rod and the second rod may be pulled away from each other such that the elastic element extends and the spacing distance increases. The elastic element may be a spring. The first rod may be rotated around its longitudinal axis in relation to the second rod. The housing may have a non-circular cross-sectional shape. The housing may have an ovular cross-sectional shape.

In another implementation, an artificial facet joint replacement system includes at least two facet joint replacement devices and a plurality of cortical screws or lateral mass screws. Each facet joint replacement device includes: (a) a housing defining a first opening, a second opening, and an internal space; (b) a first rod slidingly engaged with the first opening, the first rod including an internal end portion disposed within the internal space and an external end portion disposed outside of the internal space; (c) a second rod slidingly engaged with the second opening, the second rod including an internal end portion disposed within the internal space and an external end portion disposed outside of the internal space; and (d) an elastic element disposed within the internal space. The elastic element is coupled to and extending between the internal end portion of the first rod and the internal end portion of the second rod such that the first rod is spaced apart from the second rod by a spacing distance. Each screw is configured for coupling with a respective external end portion. Each screw is configured for fixed engagement with vertebral bone matter.

Such an artificial facet joint replacement system may optionally include one or more of the following features. The first rod and the second rod of each facet joint replacement device may be compressed toward each other such that the elastic element compresses and the spacing distance decreases. The first rod and the second rod of each facet joint replacement device may be pulled away from each other such that the elastic element extends and the spacing distance increases. The elastic element of each facet joint replacement device may be a spring. The first rod of each facet joint replacement device may be rotated around its longitudinal axis in relation to the second rod. The housing of each facet joint replacement device may have a non-circular cross-sectional shape. The housing of each facet joint replacement device may have an ovular cross-sectional shape.

In another implementation, a method of treating a spinal condition includes: (1) removing facet joint bone matter of adjacent vertebrae; (2) installing two cortical screws or lateral mass screws in each vertebrae of the adjacent vertebrae; and (3) coupling two facet joint replacement devices to the cortical screws or lateral mass screws. Each facet joint replacement device includes: (i) a housing defining a first opening, a second opening, and an internal space; (ii) a first rod slidingly engaged with the first opening, the first rod including an internal end portion disposed within the internal space and an external end portion disposed outside of the internal space; (iii) a second rod slidingly engaged with the second opening, the second rod including an internal end portion disposed within the internal space and an external end portion disposed outside of the internal space; and (iv) an elastic element disposed within the internal space, the elastic element coupled to and extending between the internal end portion of the first rod and the internal end portion of the second rod such that the first rod is spaced apart from the second rod by a spacing distance.

Such a method may optionally include one or more of the following features. The first rod and the second rod may be compressible toward each other such that the elastic element compresses and the spacing distance decreases. The first rod and the second rod can be pulled away from each other such that the elastic element extends and the spacing distance increases. The housing may have an ovular cross-sectional shape. The ovular cross-sectional shape of the housing may allow about 15 degrees of flexion/extension and about 8 degrees of lateral bending while the facet joint replacement devices are in use treating the spinal condition. The ovular cross-sectional shape of the housing may allow flexion/extension between about 10 to 20 degrees and lateral bending between about 5 to 15 degrees while the facet joint replacement devices are in use treating the spinal condition.

In another implementation, a method of treating a spinal condition includes: removing facet joint bone matter of adjacent vertebrae; installing a first cortical or lateral mass screw in an upper vertebra of the adjacent vertebrae; installing a second cortical or lateral mass screw in a lower vertebra of the adjacent vertebrae; installing a first facet joint replacement device between the first screw and the second screw; installing a third cortical or lateral mass screw in the upper vertebra; installing a fourth cortical or lateral mass screw in the lower vertebra; and installing a second facet joint replacement device between the third screw and the fourth screw.

In another implementation, an artificial facet joint replacement system includes at least two facet joint replacement devices and a plurality of cortical or lateral mass screws. Each facet joint replacement device includes: a first rod; a second rod; and an elastic element coupling the first rod with the second rod. Each screw is configured for fixed engagement with vertebral bone matter and to couple with a respective end portion of the first or second rods.

Particular embodiments of the subject matter described in this document can be implemented to realize one or more of the following advantages. In some embodiments, spinal conditions such as spondylosis, vertebral fractures, and the like can be treated using the devices and methods provided herein. The artificial facet joint devices and systems provided herein maintain the natural facet joint center of rotation. Hence, the devices and systems can be implanted to treat spinal conditions while advantageously facilitating normal stability and motions of the spine. The devices provided herein can utilize lateral mass screws (cervical spine) or cortical bone trajectory screws (thoraco-lumbar spine) rather than traditional pedicle screws. The use of such cortical screws is advantageous because they can be anchored to solid bone and preserve motion in the center of the vertebral body. Further, the use of cortical screws with the devices provided herein enables the artificial facet joints to be located near to where the natural facet joint was previously anatomically located (prior to its removal for installation of the artificial facet joint). Hence, a substantially naturally-behaving (from a biomechanical standpoint) artificial facet joint can be attained using the artificial facet joint systems provided herein. Moreover, in some embodiments, various spinal conditions can be advantageously treated in a minimally invasive fashion using the systems and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 4 is a plan view of another example artificial facet joint device in accordance with some embodiments provided herein.

FIG. 5 is a side view of the artificial facet joint device of FIG. 4.

FIG. 6 is a longitudinal cross-sectional view of the artificial facet joint device of FIG. 4.

FIG. 12 is a plan view of another example artificial facet joint device in accordance with some embodiments provided herein.

FIG. 13 is a longitudinal cross-sectional view of the artificial facet joint device of FIG. 12.

FIG. 14 is a perspective side view of the artificial facet joint device of FIG. 12.

FIG. 15 is a plan view of another example artificial facet joint device in accordance with some embodiments provided herein.

FIG. 16 is a plan view of another example artificial facet joint device in accordance with some embodiments provided herein.

FIG. 17 is a plan view of another example artificial facet joint device in accordance with some embodiments provided herein.

FIG. 18 is a perspective view of another example artificial facet joint device in accordance with some embodiments provided herein.

FIG. 19 is a longitudinal cross-sectional view of the artificial facet joint device of FIG. 18.

FIG. 20 is an end view of the artificial facet joint device of FIG. 18.

FIG. 23 is a side view of another example artificial facet joint device in accordance with some embodiments provided herein.

FIGS. 24 and 25 are a sectional views of the artificial facet joint device of FIG. 23.

Like reference numbers represent corresponding parts throughout.

DETAILED DESCRIPTION

This document provides devices and systems for treating spinal conditions. For example, this document provides artificial facet joint systems that can be implanted to treat spinal conditions while facilitating normal stability and motions of the spine (including limitations to such motions). The systems and methods provided herein can be used to treat spinal conditions such as, but not limited to, spondylosis, spondylolisthesis, spinal stenosis, foraminal stenosis, vertebral fractures, osteoporosis, and the like.

The facet joints play a pivotal role in spinal biomechanics. In the lumbar and cervical spine, the major role of the facet joint is to allow for flexion and extension. To a lesser degree, lateral bending and axial rotation also occur about this joint. In some cases, the facet joint can carry up to 25% of a spinal axial compression load.

In view of the facts above, artificial facet joint devices would preferentially allow for the following motions: flexion, extension, lateral bending, axial compression, axial tension, and axial rotation. Moreover, it is desirable to use a device that can achieve such motions while also maintaining the natural facet joint center of rotation and natural limitations on such motions.

This disclosure describes facet joint replacement (FJR) systems that would allow surgeons to perform an inferior facetectomy (a common procedure in both the cervical and lumbar spine) or similar surgical technique in which the natural facet joints would be removed and effectively replaced with an artificial facet joint. Such artificial FJR systems will preserve to a first order approximation the natural biomechanics of the facet joint.

Figure 1:
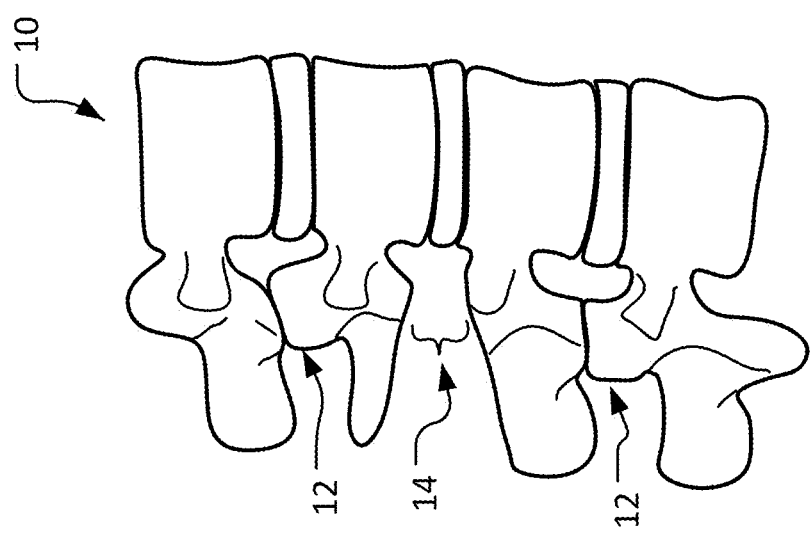
FIG. 1 is a lateral view of a portion of a spine that has had facet joints surgically removed in preparation for the installation of artificial facet joints.

Referring to FIG. 1, a portion of a spine 10 can be prepared to receive an artificial FJR system as provided herein. In this example, the spinal portion 10 has undergone an inferior facetectomy. In some cases, other similar surgical techniques in which the facet joints, or portions thereof, are removed can be performed in preparation to receive an artificial FJR system as provided herein.

Spinal portion 10 includes natural facet joints 12. However, in this example spinal portion 10 has facet joints removed in region 14. The removal of the natural facet join in region 14 can be performed in preparation for the installation of an artificial FJR system as provided herein. In some cases, the removal of the natural facet joint in region 14 can be performed in a minimally-invasive manner.

Figure 2:
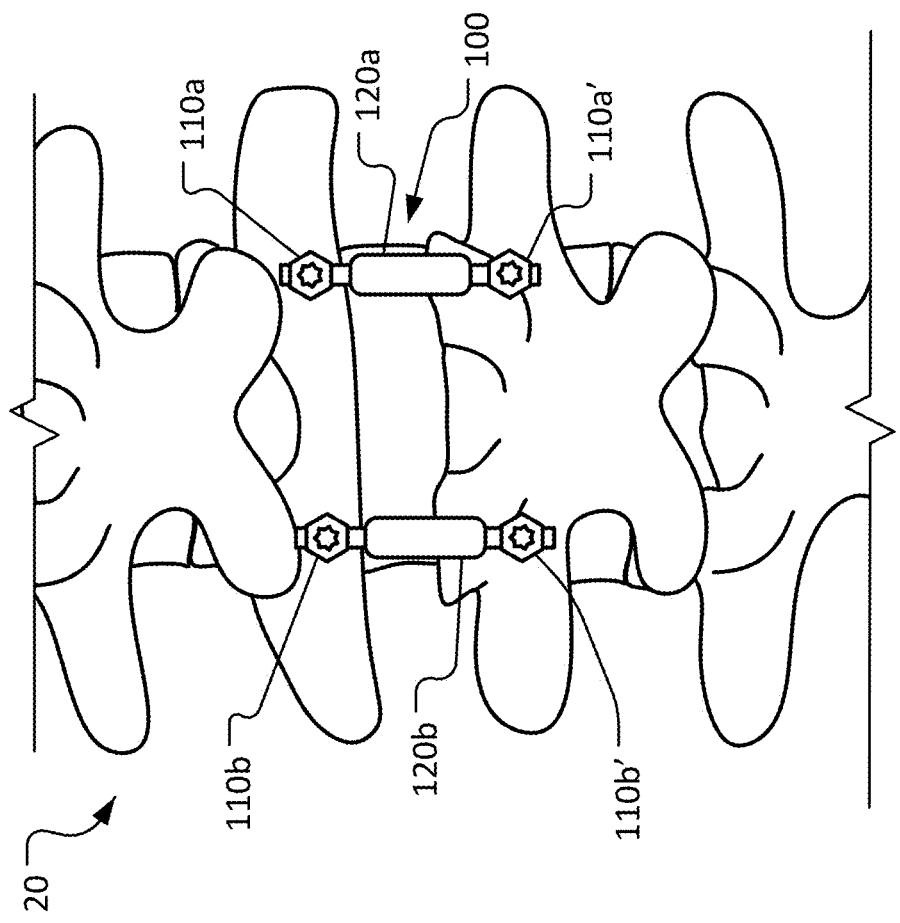
FIG. 2 is a perspective view of a portion of a spine in which an example artificial facet joint system has been installed in accordance with some embodiments provided herein.

Referring to FIG. 2, an example artificial FJR system 100 can be installed in a spinal portion 20 to substitute for the function of a removed natural facet joint. Artificial FJR system 100 can be implanted to treat spinal conditions while facilitating substantially normal stability and motions of the spine 20. In some cases, in addition to installing artificial FJR system 100, one or more prosthetic elements that simulate intervertebral discs can be installed between adjacent vertebrae.

In some cases, artificial FJR system 100 can allow for the following motions: flexion, extension, lateral bending, axial compression, axial tension, and rotation. In addition, artificial FJR system 100 can facilitate such motions while also substantially maintaining the natural facet joint center of rotation.

In some embodiments, artificial FJR system 100 is structurally designed to allow limited amounts of displacement related to the aforementioned motions. Moreover, in some embodiments the resistance provided by artificial FJR system 100 to displacements from such motions can be linear, or non-linear. For example, in some embodiments non-linear resistance to displacements can be provided by artificial FJR system 100 such that the resistance substantially increases as the structural limitations on the displacements are neared.

In the depicted embodiment, artificial FJR system 100 includes a first pair of cortical trajectory screws (cortical screws) 110a and 110a', a first facet joint replacement device 120a, a second pair of cortical screws 110b and 110b', and a second facet joint replacement device 120b. First facet joint replacement device 120a is fixedly joined to, and extending between, cortical screw 110a and cortical screw 110a'. Second facet joint replacement device 120b is fixedly joined to, and extending between, cortical screw 110b and cortical screw 110b'.

In some cases, cortical screws 110a, 110a', 110b, and 110b' can be the same as, or similar to, the types of cortical screws that are installed along with rods as part of a spinal fusion system. The cortical screws 110a, 110a', 110b, and 110b' may also be referred to as cortical bone trajectory screws (for thoracolumbar applications) and lateral mass screws (for cervical applications). One example of such cortical screws (for thoracolumbar) is the VIPER® Cortical Fix Screw from DePuy Synthes (a Johnson & Johnson company) can be used for this application. One example of lateral mass screws (for cervical applications) is the MOUNTAINEER® OCT Spinal System also from DePuy Synthes. Other companies make similar screws. Such cortical screws 110a, 110a', 110b, and 110b' can be installed (i.e., affixed to vertebrae) using a minimally-invasive surgical procedure in some cases. Other types of fixation devices can additionally or alternatively be used.

Facet joint replacement devices 120a and 120b extend between first pair of cortical screws 110a and 110a' and second pair of cortical screws 110b and 110b' respectively. Facet joint replacement devices 120a and 120b thereby replace the function of the natural facet joints that have been removed to make room to install artificial FJR system 100. As described further below, facet joint replacement devices 120a and 120b are designed with multiple degrees of freedom, and with certain physical constraints on those degrees of freedom, so as to mimic the functions and range of motion of natural facet joints.

In some embodiments, one or more laterally-extending stabilizing members (not shown) can be installed between facet joint replacement devices 120a and 120b. The stabilizing members can be completely rigid or can be somewhat flexible. In some embodiments, a single stabilizing member is included that extends between mid-body portions of facet joint replacement devices 120a and 120b. In some embodiments, such stabilizing members are installed in an x-pattern (i.e., a first stabilizing member extends between cortical screws 110a and 110b', and a second stabilizing member extends between 110b and 110a').

Figure 3:
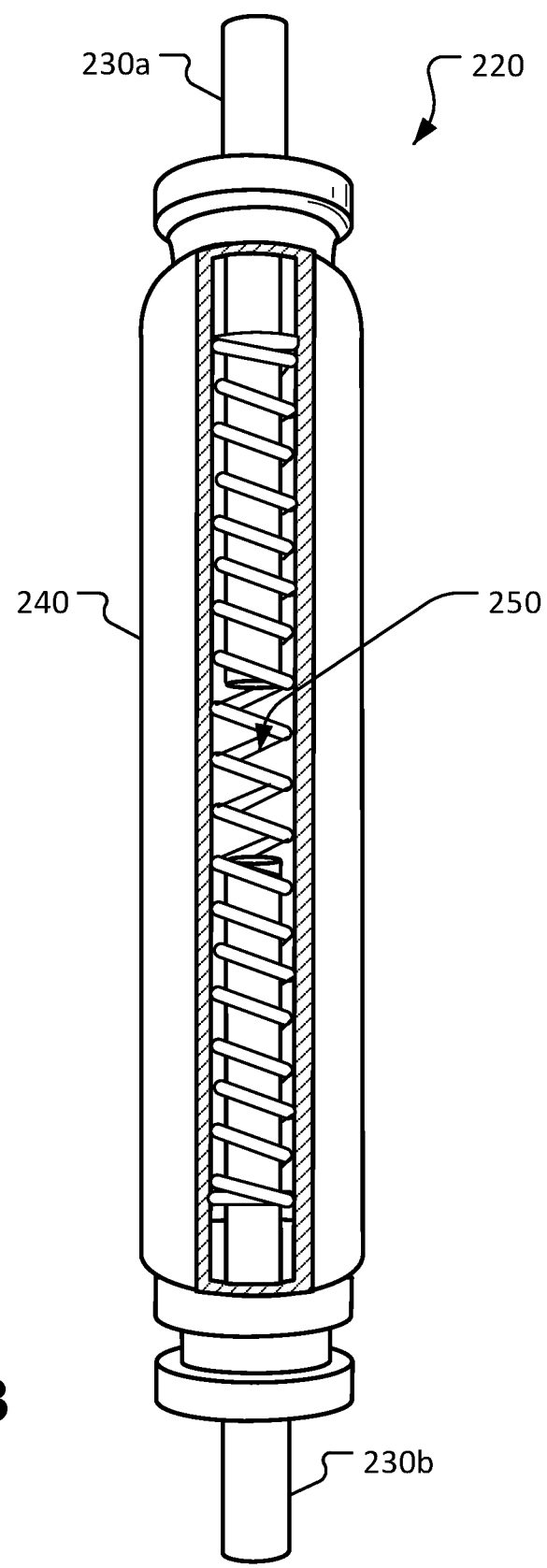
FIG. 3 is a side view of an example artificial facet joint device in accordance with some embodiments provided herein.

Referring also to FIG. 3, a facet joint replacement device 220 is an example of the types of facet joint replacement devices that can be used with artificial FJR system 100. In the depicted embodiment, facet joint replacement device 220 includes a first rod 230a, a second rod 230b, a housing 240, and an elastic element 250. In this example, elastic element 250 is a coil spring.

Housing 240 is an elongate member that defines an internal space. End portions of rods 230a and 230b are movably disposed within the internal space of housing 240. Also, elastic element 250 is disposed within the internal space of housing 240.

Housing 240 can be made of various biocompatible metallic or polymeric materials. For example, housing 240 can be made of materials such as, but not limited to, stainless steel, titanium, titanium alloys, cobalt-chrome, nitinol, polyetheretherketone (PEEK), polytetrafluoroethylene (PTFE), perfluoroalkoxy alkanes (PFA), polyvinylidene difluoride (PVDF), and the like, and combinations thereof. In some cases, housing 240 is made by a molding process. In some cases, housing 240 is made by a machining process. In some embodiments, one or more inserts may be installed in or on housing 240. In some cases, housing 240 and/or one or more other components of facet joint replacement device 220 is made by a 3D printing method. In some such cases, the design of the component(s) can be customized for a particular patient's spinal anatomy as defined by MR or CT imaging modalities.

Housing 240 can have various cross-sectional shapes. In some embodiments, the cross-sectional shape of the internal space defined by housing 240 is circular, ovular, elliptical, polygonal, and the like. In the depicted embodiment, the cross-sectional shape of housing 240 is an oval. That is, the cross-sectional shape of the internal space is ovular. The cross-sectional shape of the internal space can be selected to allow for a certain amount of free play between rods 230a and 230b and the internal wall of housing 240. In some embodiments, housing 240 is designed to have some degree of compliance such that housing 240 can bend or flex while in use. In some embodiments, housing 240 is designed to be rigid such that housing 240 substantially does not bend or flex while in use.

In the depicted embodiment having an ovular cross-sectional shape, differing amounts of free play between rods 230a and 230b and the internal wall of housing 240 exist in different axes of motion. For example, in the depicted embodiment the ovular cross-sectional shape allows for free play between rods 230a and 230b and the internal wall of housing 240 such that about 15 degrees of flexion/extension and about 8 degrees of lateral bending is possible while facet joint replacement device 220 is in use. It should be understood that the amounts of free play between rods 230a and 230b and the internal wall of housing 240 can be selected to attain basically any other desired degrees of flexion/extension and lateral bending. In some embodiments, the ovular cross-sectional shape of the housing allows flexion/extension between about 10 to 20 degrees and lateral bending between about 5 to 15 degrees while the facet joint replacement devices are in use treating the spinal condition.

Rods 230a and 230b are slidingly engaged with respective openings defined at the ends of housing 240. End portions of rods 230a and 230b are disposed outside of the internal space defined by housing 240. In some embodiments, bushings may be coupled to housing 240 and configured to facilitate the sliding engagement between housing 240 and rods 230a and 230b. In the depicted embodiment, the cross-sectional shape of rods 230a and 230b are circular. In some embodiments, rods 230a and 230b can have other cross-sectional shapes such as, but not limited to, ovular, elliptical, polygonal, and the like. Rods 230a and 230b can be made from any of the materials described above in regard to housing 240.

In some embodiments, rods 230a and 230b can rotate around their longitudinal axes in relation to housing 240. In the depicted embodiment, rods 230a and 230b are restrained from rotating around their longitudinal axes in relation to housing 240.

Facet joint replacement device 220 also includes elastic element 250. Elastic element 250 is coupled to and extends between the internal end portions of rods 230a and 230b. Accordingly, the internal end portions of rods 230a and 230b are spaced apart from each other by a spacing distance in which elastic element 250 resides. In some embodiments, at least a portion of elastic element 250 is fixedly coupled to the internal end portions of rods 230a and/or 230b.

The spacing distance allows translational movement of rod 230a in relation to rod 230b. That is, first rod 230a and second rod 230b can be compressed toward each other such that elastic element 250 compresses and the spacing distance decreases. In addition, first rod 230a and second rod 230b can be pulled away from each other such that elastic element extends 250 and the spacing distance increases.

Elastic element 250 can be made of various materials and can be constructed in various manners. In some embodiments, such as the depicted embodiment, elastic element 250 is a spring. In some embodiments, elastic element 250 is made of a mesh composite. In some embodiments, elastic element 250 is an elastic polymeric element.

Any one of the types and variations of facet joint replacement devices described herein can be used with artificial FJR system 100. Artificial FJR system 100 can be installed in a spinal portion 20 to substitute for the function of a removed natural facet joint. Artificial FJR system 100 can be implanted to treat spinal conditions while facilitating substantially normal stability and motions of the spine 20.

Referring to FIGS. 4-6, another exemplary facet joint replacement device 300 can be installed, for example, in the manner described regarding artificial FJR system 100 (FIG. 2). Facet joint replacement device 300 includes a first rod 310a, an opposing second rod 310b, a housing 320, and an elastic member 330. Rods 310a and 310b can be coupled with cortical screws or lateral mass screws in situ. The materials used to construct the components of facet joint replacement device 300 can be analogous to the materials described above in reference to facet joint replacement device 220.

Rods 310a and 310b are slidably coupled with housing 320. That is, rods 310a and 310b can extend and retract along their longitudinal axes in relation to housing 320. In some embodiments, the mechanical fit between the outer peripheries of rods 310a and 310b and the respective openings of housing 320 are designed to allow for a limited amount of lateral and/or rotational motion of rods 310a and 310a (e.g., so as to mimic the natural biomechanics of natural facet joints).

The inner end portions of rods 310a and 310b are fixedly coupled with elastic member 330 in an opposing orientation. Therefore, as rods 310a and/or 310b extend or retract in relation to housing 320, elastic member 330 is strained correspondingly. Such strain of elastic member 330 elastically resists the extension or retraction of rods 310a and 310b. In some embodiments, elastic member 330 also resists rotary and lateral bending motions of rods 310a and 310b.

Elastic member 330 can be made of a variety of different types of materials and combinations of materials. For example, elastic member 330 can be made of polymeric materials such as, but not limited to, polyurethane, polyethylene, silicone, and other biocompatible elastomers. In some embodiments, elastic member 330 can be made of metallic materials such as, but not limited to, nitinol, stainless steel, titanium, titanium alloys, cobalt-chrome, and the like. In some embodiments, elastic member 330 is solid, but in other embodiments elastic member 330 is constructed for enhanced compliance and/or elasticity. For example, in some embodiments elastic member 330, or portions thereof, is molded, laser-cut, machined, braided, woven, etc. so that the compliance and/or elasticity of elastic member 330 is enhanced.

In the depicted embodiment, housing 320 defines an open interior space 322 in which elastic member 330 and inward portions of rods 310a and 310b are disposed. Open interior space 322 is oblong-shaped in this example, but other shapes are also envisioned, e.g., cylindrical, elliptical, ovular, spherical, three-dimensional polygonal shapes, and the like.

The shape of elastic member 330 is an annular cylinder, in the depicted example. In some embodiments, elastic member 330 is toroidal, cubical, a polyhedron, and the like.

The combination of the shape of interior space 322 and the shape of elastic member 330 can be strategically selected to facilitate a desired limited degree of movement of rods 310a and 310b, and/or a desired particular amount of resistance to such movements. It should be understood that such factors can be selectively adjusted to tune the facet joint replacement device 300 to perform like a natural facet joint, or to perform in any other manner as desired.

Figure 8:
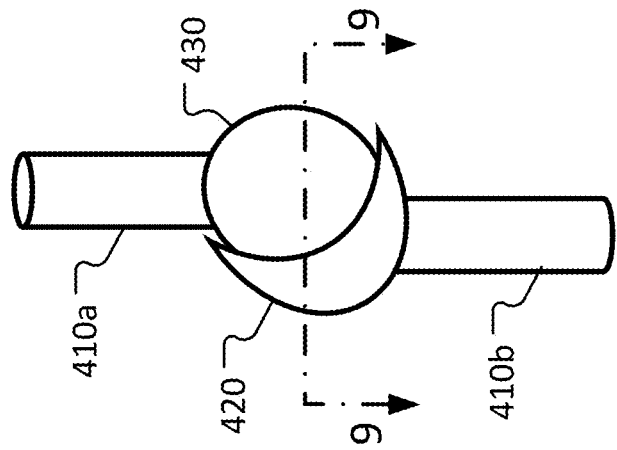
FIG. 8 is a side view of the artificial facet joint device of FIG. 7.
Figure 9:
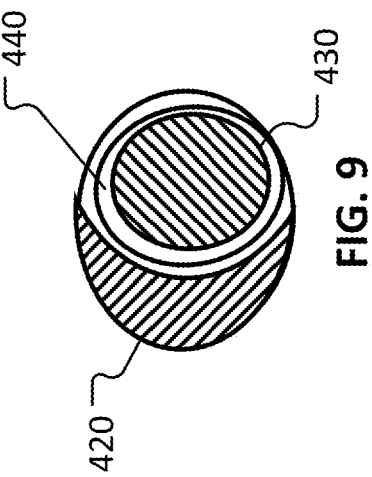
FIG. 9 is a transverse cross-sectional view of the artificial facet joint device of FIG. 7.
Figure 7:
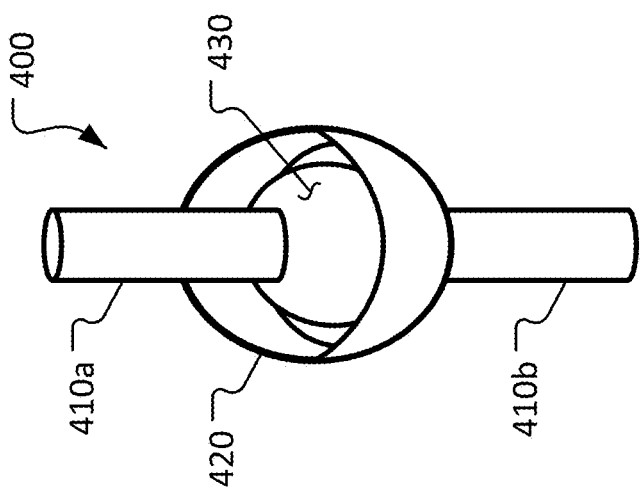
FIG. 7 is a perspective view of another example artificial facet joint device in accordance with some embodiments provided herein.

Referring to FIGS. 7-9, another exemplary facet joint replacement device 400 can be installed, for example, in the manner described regarding artificial FJR system 100 (FIG. 2). Facet joint replacement device 400 includes a first rod 410a, an opposing second rod 410b, a socket member 420, and a spherical member 430. Rods 410a and 410b can be coupled with cortical screws or lateral mass screws in situ. The materials used to construct the components of facet joint replacement device 400 can be analogous to the materials described above in reference to facet joint replacement device 220.

Socket member 420 defines a spherical open interior space in which spherical member 430 is disposed. The mechanical fit between socket member 420 and spherical member 430 allows for relative rotary movements therebetween in a ball-in-socket joint manner. The rotary motion allowed by facet joint replacement device 400 facilitates anatomical movements (i.e., to a certain extent) such as extension, flexion, lateral bending, and rotation. The desired allowed motions can be selected and facet joint replacement device 400 can be designed accordingly.

In the depicted embodiment, spherical member 430 is movably constrained within socket member 420. That is, while relative rotary motion is allowed between spherical member 430 and socket member 420, spherical member 430 cannot separate from socket member 420. In some embodiments, an optional liner 440 (FIG. 9) is included between spherical member 430 and socket member 420. Liner 440 can be a polymeric material that decreases friction and wear between spherical member 430 and socket member 420, for example. In some embodiments, no such liner 440 is included.

Figure 11:
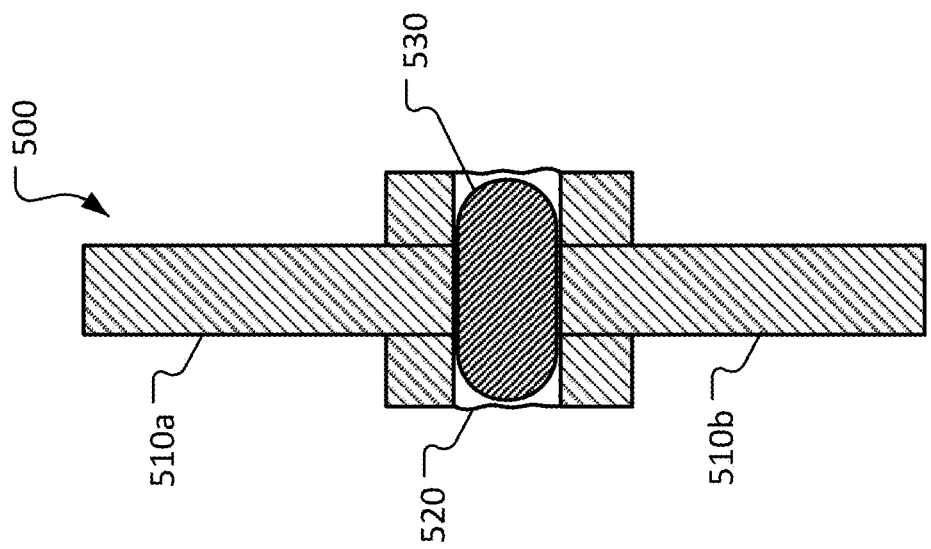
FIG. 11 is a longitudinal cross-sectional view of the artificial facet joint device of FIG. 10.
Figure 10:
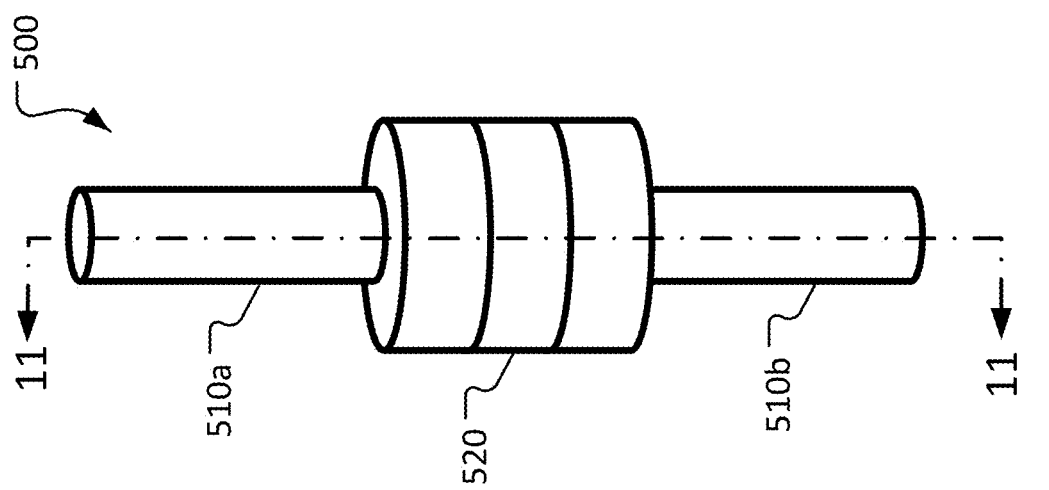
FIG. 10 is a perspective view of another example artificial facet joint device in accordance with some embodiments provided herein.

Referring to FIGS. 10 and 11, another exemplary facet joint replacement device 500 can be installed, for example, in the manner described regarding artificial FJR system 100 (FIG. 2). Facet joint replacement device 500 includes a first rod 510a, an opposing second rod 510b, a flexible-walled housing 520, and an elastic member 530. Rods 510a and 510b can be coupled with cortical screws or lateral mass screws in situ. The materials used to construct the components of facet joint replacement device 500 can be analogous to the materials described above in reference to facet joint replacement device 220.

That is, rods 510a and 510b can extend and retract along their longitudinal axes by a limited amount. Further, rods 510a and 510b are allowed a limited amount of lateral and/or rotational motion (e.g., to mimic the natural biomechanics of natural facet joints).

Elastic member 530 opposes movements of rods 510a and 510b. Therefore, as rods 510a and/or 510b extend or retract in relation to housing 520, elastic member 530 is strained correspondingly. Such strain of elastic member 530 elastically resists the extension or retraction of rods 510a and 510b, and also resists rotary and lateral bending motions of rods 510a and 510b (e.g., to mimic the natural biomechanics of natural facet joints).

In the depicted embodiment, elastic member 530 is disposed within an interior space defined by flexible-walled housing 520. The walls of flexible-walled housing 520 are flexible to facilitate the above-described motions of rods 510a and 510b. In some embodiments, flexible-walled housing 520 is made of a film, a woven material, a knitted material, and the like. Flexible-walled housing 520 can be made of materials such as, but not limited to, PTFE, ePTFE, DACRON® and the like.

Referring to FIGS. 12-14, another exemplary facet joint replacement device 600 can be installed, for example, in the manner described regarding artificial FJR system 100 (FIG. 2). Facet joint replacement device 600 includes a first rod 610a, an opposing second rod 610b, a first housing portion 620a, a second housing portion 620b, and an elastic member 630. Rods 610a and 610b can be coupled with cortical screws or lateral mass screws in situ. The materials used to construct the components of facet joint replacement device 600 can be analogous to the materials described above in reference to facet joint replacement device 220.

Facet joint replacement device 600 is designed to allow rods 610a and 610b to extend and retract limited amounts in relation to housing portions 620a and 620b respectively. For example, as visible in FIG. 13, inner end portions of rods 610a and 610b are disposed within spaces defined by housing portions 620a and 620b respectively. An elastomer can be disposed within the spaces defined by housing portions 620a and 620b. Therefore, the elastomer disposed within the spaces defined by housing portions 620a and 620b will allow (while resisting) extension and retraction of rods 610a and 610b.

Facet joint replacement device 600 is also designed to allow rods 610a and 610b to rotate or pivot in relation to each other. For this purpose, an elastic element 630 is attached between housing portions 620a and 620b. In that configuration, elastic element 630 will allow (while providing some resistance) relative rotation, bending, and torsion of rods 610a and 610b.

Referring to FIG. 15, another exemplary facet joint replacement device 700 can be installed, for example, in the manner described regarding artificial FJR system 100 (FIG. 2). Facet joint replacement device 700 includes a first end portion 710a, an opposing second end portion 710b, and a middle portion 720. End portions 710a and 710b can be coupled with cortical screws or lateral mass screws in situ.

In the depicted embodiment, facet joint replacement device 700 is a monolithic construct. That is, the entirety of facet joint replacement device 700 is made of a single type of material with uniform mechanical properties throughout.

Facet joint replacement device 700 is a pliable element. In some embodiments, facet joint replacement device 700 is a pliable tube. In some embodiments, facet joint replacement device 700 is a pliable solid rod. The pliability (flexibility) allows for extension, compression, rotation, and bending of facet joint replacement device 700 to a limited extent (and while providing resistance). In some embodiments, the design of facet joint replacement device 700 can be optimized for facilitating certain types of motions while constraining other types of motions.

In some cases, facet joint replacement device 700 can be made of a mesh material, a laser-cut and expanded material, a braided material, an etched material, a machined material, a woven material, a single-wire material, a multi-wire material, and combinations thereof. In some embodiments, facet joint replacement device 700 can be constructed from metallic materials such as, but not limited to, titanium, nitinol, cobalt chrome, stainless steel, and the like, and combinations thereof. In some embodiments, facet joint replacement device 700 can be constructed from polymeric materials such as, but not limited to, silicone, DELRIN®, nylon, acrylonitrile butadiene styrene (ABS), polyester, and the like.

Referring to FIG. 16, another exemplary facet joint replacement device 800 can be installed, for example, in the manner described regarding artificial FJR system 100 (FIG. 2). Facet joint replacement device 800 includes a first rod 810a, an opposing second rod 810b, and a flexible middle portion 820. Rods 810a and 810b can be coupled with cortical screws or lateral mass screws in situ.

In some embodiments, rods 810a and 810b are solid members (e.g., made of titanium or other metallic materials described herein). Flexible middle portion 820, on the other hand, can be a construct like facet joint replacement device 700. That is, flexible middle portion 820 can be, for example, a mesh material, a laser-cut and expanded material, a braided material, an etched material, a machined material, a woven material, a single-wire material, a multi-wire material, and combinations thereof. Flexible middle portion 820 allows for extension, compression, rotation, and bending of facet joint replacement device 800 to a limited extent (and while providing resistance), while rods 810a and 810b do not, of themselves, allow for such movements.

Referring to FIG. 17, another exemplary facet joint replacement device 900 can be installed, for example, in the manner described regarding artificial FJR system 100 (FIG. 2). Facet joint replacement device 900 includes a first pliable rod 910a, an opposing second pliable rod 910b, and a flexible middle portion 920. Pliable rods 910a and 910b can be coupled with cortical screws or lateral mass screws in situ.

Facet joint replacement device 900 is similar to facet joint replacement device 800 except that pliable rods 910a and 910b are flexible members. Said differently, whereas facet joint replacement device 700 (FIG. 15) is a monolithic construct, facet joint replacement device 900 is a composite construct.

Pliable rods 910a and 910b, and flexible middle portion 920 can be constructed using materials and techniques like that of facet joint replacement device 700. However, pliable rods 910a and 910b are constructed to have different mechanical properties than flexible middle portion 920. For example, in some embodiments, pliable rods 910a and 910b have a lower modulus of elasticity than flexible middle portion 920. The properties of pliable rods 910a and 910b, and flexible middle portion 920 can be strategically selected to mimic the natural biomechanical motions, motion limits, and resistance to motion like a natural facet joint.

Referring to FIGS. 18-20, another exemplary facet joint replacement device 1000 can be installed, for example, in the manner described regarding artificial FJR system 100 (FIG. 2). Facet joint replacement device 1000 includes a first rod 1010a, an opposing second rod 1010b, and a middle ball-and-socket portion 1020 from which rods 1010a and 1010b extend. Rods 1010a and 1010b can be coupled with cortical screws or lateral mass screws in situ. The materials used to construct the components of facet joint replacement device 1000 can be analogous to the materials described above in reference to facet joint replacement device 220, for example.

Ball-and-socket portion 1020 includes a housing 1022 that defines an open interior space in which a socket member 1030 is disposed. Socket member 1030, in turn, defines a spherical open interior space (with an open end). A spherical member 1012 is movably disposed within the spherical open interior space defined by socket member 1030. First rod 1010a is coupled to spherical member 1012. Second rod 1010b is coupled to housing 1022.

Socket member 1030 can be made of an elastomer or polymeric material in some embodiments. For example, socket member 1030 can be made of polymeric materials such as, but not limited to, polyurethane, polyethylene, ultra-high-molecular-weight polyethylene, silicone, polytetrafluoroethylene, and other biocompatible elastomers. Socket member 1030 can serve to decrease friction and wear between spherical member 1012 and housing 1022, for example. The mechanical fit (e.g., a close slip fit or a slight interference fit in some embodiments) between socket member 1030 and spherical member 1012 allows for relative rotary movements therebetween in a ball-in-socket joint manner.

The rotary motion allowed by facet joint replacement device 1000 facilitates anatomical movements (i.e., to a certain extent) such as extension, flexion, lateral bending, and rotation. The desired allowed motions can be selected and facet joint replacement device 1000 can be designed accordingly to facilitate such desired allowed motions. For example, housing 1022 defines an opening 1024 through which first rod 1010a extends. The shape of opening 1024 can be selected to limit the range of some motions such as extension, flexion, and lateral bending. For example, in the depicted embodiment opening 1024 is ovular so that some types of movements (e.g., in particular directions such as flexion, extension, and/or lateral bending) are restricted more than others (e.g., to mimic natural spinal movements).

In some embodiments, opening 1024 is defined by a separate member (e.g., a retainer clip) that is removable from housing 1022. The use of such a removable member that defines opening 1024 can also facilitate assembly of ball-and-socket portion 1020 (e.g., such that spherical member 1012 can be larger in diameter than the diameter of opening 1024).

In the depicted embodiment, spherical member 1012 is movably constrained within socket member 1030 such that facet joint replacement device 1000 will not become separated. That is, while relative rotary motion is allowed between spherical member 1012 and socket member 1030, spherical member 1012 cannot become dislodged from socket member 1030. That is the case because spherical member 1012 is larger in diameter than the diameter of opening 1024.

While the depicted embodiment includes socket member 1030 made of an elastomer or polymeric material, in some embodiments no such socket member 1030 is included between spherical member 1012 and housing 1022. In such a case, housing 1022 can define a spherical open interior space that closely receives spherical member 1012.

Figure 21:
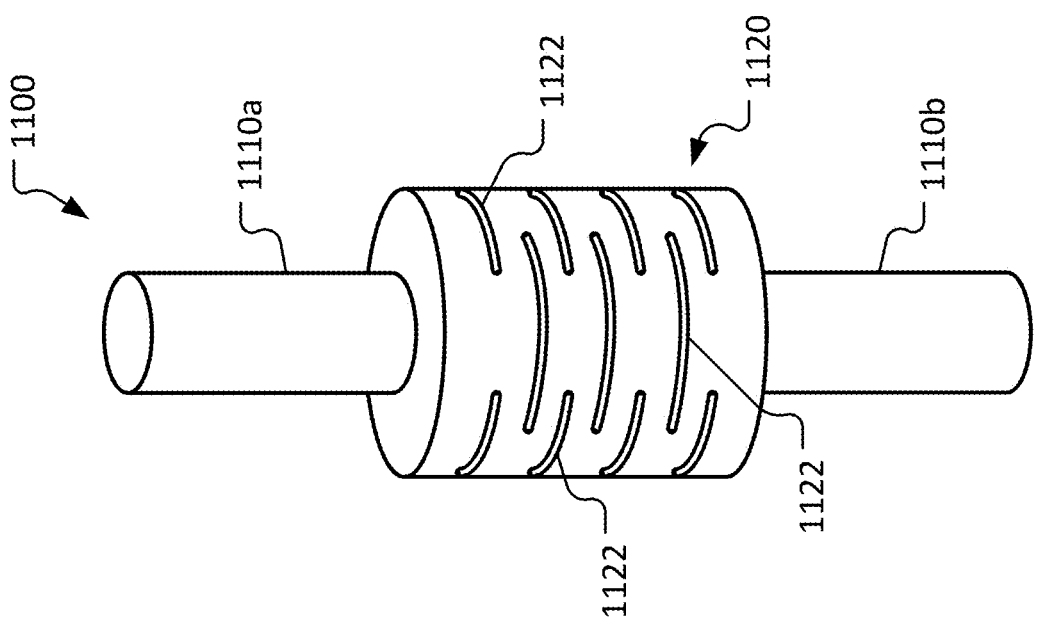
FIG. 21 is a perspective view of another example artificial facet joint device in accordance with some embodiments provided herein.

Referring to FIG. 21, another exemplary facet joint replacement device 1100 can be installed, for example, in the manner described regarding artificial FJR system 100 (FIG. 2). Facet joint replacement device 1100 includes a first rod 1110*a*, an opposing second rod 1110*b*, and a flexible middle portion 1120 from which rods 1110*a* and 1110*b* extend. Rods 1110*a* and 1110*b* can be coupled with cortical screws or lateral mass screws in situ.

Flexible middle portion 1120 allows for extension, compression, rotation, and bending of facet joint replacement device 1100 to a limited extent (and while providing resistance), while rods 1110*a* and 1110*b* do not, of themselves, allow for such movements.

In some embodiments, rods 1110*a* and 1110*b* are solid members (e.g., made of titanium, stainless steel, or other metallic materials described herein). Flexible middle portion 1120, can also be made of such materials (and/or of other materials such as polymeric materials). Moreover, in some examples facet joint replacement device 1100 is a unitary construct (e.g., made from a single piece of precursor material). In some examples, rods 1110*a*, 1110*b* and flexible middle portion 1120 are made as separate components that are assembled together to make facet joint replacement device 1100.

Flexible middle portion 1120 includes multiple slots 1122 that are cut into flexible middle portion 1120 to increase the flexibility of flexible middle portion 1120. It should be understood that the size (e.g., depth, width, length) and positioning (e.g., spacing, direction, location, etc.) of slots 1122 can be selected to allow for a desired extent of extension, compression, rotation, and/or bending of facet joint replacement device 1100 to a limited extent (and while providing resistance). In some embodiments, slots 1122 can be filled with a compliant elastomeric material to inhibit tissue ingrowth.

Figure 22:
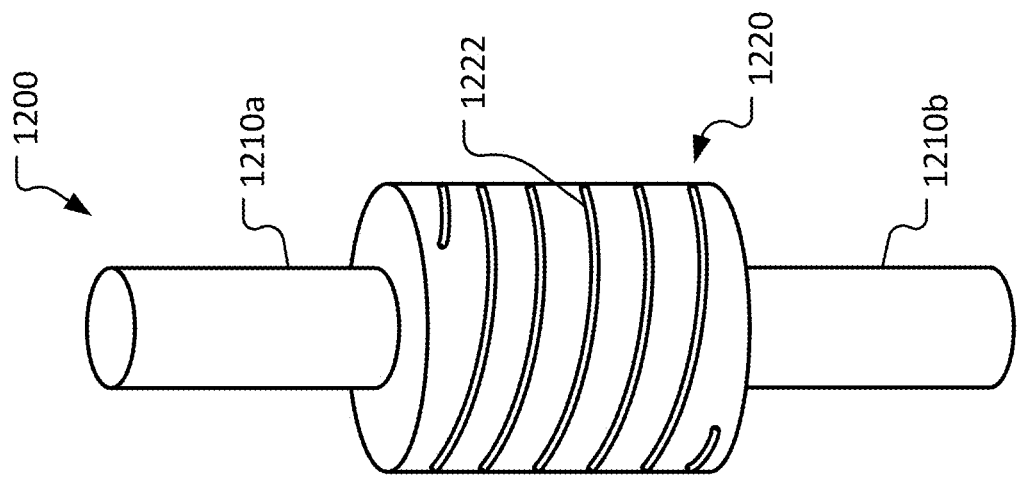
FIG. 22 is a perspective view of another example artificial facet joint device in accordance with some embodiments provided herein.

Referring to FIG. 22, another exemplary facet joint replacement device 1200 can be installed, for example, in the manner described regarding artificial FJR system 100 (FIG. 2). Facet joint replacement device 1200 includes a first rod 1210*a*, an opposing second rod 1210*b*, and a flexible middle portion 1220 from which rods 1210*a* and 1210*b* extend. Rods 1210*a* and 1210*b* can be coupled with cortical screws or lateral mass screws in situ.

Flexible middle portion 1220 allows for extension, compression, rotation, and bending of facet joint replacement device 1200 to a limited extent (and while providing resistance), while rods 1210*a* and 1210*b* do not, of themselves, allow for such movements.

In some embodiments, rods 1210*a* and 1210*b* are solid members (e.g., made of titanium, stainless steel, or other metallic materials described herein). Flexible middle portion 1220, can also be made of such materials (and/or of other materials such as polymeric materials). Moreover, in some examples facet joint replacement device 1200 is a unitary construct (e.g., made from a single piece of precursor material). In some examples, rods 1210*a*, 1210*b* and flexible middle portion 1220 are made as separate components that are assembled together to make facet joint replacement device 1200.

Flexible middle portion 1220 includes a spiral slot 1222 that is cut into flexible middle portion 1220 to increase the flexibility of flexible middle portion 1220. It should be understood that the size (e.g., depth, width, length) and positioning (e.g., spacing, direction, location, etc.) of slot 1222 can be selected to allow for a desired extent of extension, compression, rotation, and/or bending of facet joint replacement device 1200 to a limited extent (and while providing resistance). While the depicted embodiment includes a single spiral slot 1222, in some embodiments two or more distinct spiral slots 1222 are included. In some embodiments, slots 1122 can be filled with a compliant elastomeric material to inhibit tissue ingrowth.

Referring to FIGS. 23-25, another exemplary facet joint replacement device 1300 can be installed, for example, in the manner described regarding artificial FJR system 100 (FIG. 2). Facet joint replacement device 1300 includes a first rod 1310*a*, an opposing second rod 1310*b*, a first housing portion 1320*a*, a second housing portion 1320*b*, and an elastic member 1330. Rods 1310*a* and 1310*b* can be coupled with cortical screws or lateral mass screws in situ. Rods 1310*a* and 1310*b* can be non-linear (such as in the depicted embodiment) to allow for the free end portions of rods 1310*a* and 1310*b* to be approximately coaxial while the ends of rods 1310*a* and 1310*b* that are attached to housing portions 1320*a* and 1320*b* to be offset from each other. The materials used to construct the components of facet joint replacement device 1300 can be analogous to the materials described above in reference to facet joint replacement devices 220 and 600, for example.

Facet joint replacement device 1300 is designed to allow rods 1310*a* and 1310*b* to extend and retract limited amounts in relation to housing portions 1320*a* and 1320*b* respectively. For example, as visible in FIGS. 24 and 25, inner end portions 1312*a* and 1312*b* (not shown) of rods 1310*a* and 1310*b* are disposed within open spaces 1312*a* and 1312*b* (not shown) defined by housing portions 1320*a* and 1320*b* respectively. Spaces 1312*a* and 1312*b* are larger than inner end portions 1312*a* and 1312*b* to allow a limited freedom of movement (e.g., longitudinal extension/retraction for flexion and extension, axial rotation, and some lateral bending) of rods 1310*a* and 1310*b* relative to housing portions 1320*a* and 1320*b* respectively. In some embodiments, an elastomer can be disposed within the spaces 1312*a* and 1312*b*. Therefore, the elastomer disposed within the spaces defined by housing portions 1320*a* and 1320*b* will allow (while resisting) extension and retraction of rods 1310*a* and 1310*b*.

Facet joint replacement device 1300 is also designed to allow rods 1310*a* and 1310*b* to rotate or pivot in relation to each other (e.g., for lateral bending). For this purpose, an elastic element 1330 is attached between housing portions 1320*a* and 1320*b*. In that configuration, elastic element 1330 will allow (while providing some resistance) relative rotation (for lateral bending), bending (for flexion/extension), and torsion of rods 1310*a* and 1310*b*.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A facet joint replacement device, comprising:
   a housing defining a first opening, a second opening, and an internal space;
   a first rod having a longitudinal axis and a circular cross-sectional shape, the first rod slidingly engaged with the first opening, the first rod including an internal end portion disposed within the internal space and an external end portion disposed outside of the internal space;
   a second rod having a longitudinal axis and a circular cross-sectional shape, the second rod slidingly engaged with the second opening, the second rod including an internal end portion disposed within the internal space and an external end portion disposed outside of the internal space; and
   an elastic element disposed within the internal space, the elastic element coupled to and extending between the internal end portion of the first rod and the internal end portion of the second rod such that the first rod is spaced apart from the second rod by a spacing distance, wherein a longitudinal cross-sectional shape of the internal space taken along the longitudinal axes is ovular.

2. The facet joint replacement device of claim 1, wherein the first rod and the second rod can be compressed toward each other such that the elastic element compresses and the spacing distance decreases.

3. The facet joint replacement device of claim 2, wherein the first rod and the second rod can be pulled away from each other such that the elastic element extends and the spacing distance increases.

4. The facet joint replacement device of claim 1, wherein the elastic element is a spring.

5. The facet joint replacement device of claim 1, wherein the first rod can be rotated around its longitudinal axis in relation to the second rod.

6. The facet joint replacement device of claim 1, wherein the housing is a molded component.

7. The facet joint replacement device of claim 1, wherein the first and second rods can rotate relative to the housing.

8. The facet joint replacement device of claim 1, wherein the first and second rods are restrained from rotating relative to the housing.

9. The facet joint replacement device of claim 1, wherein the elastic element is a polymeric element.

10. A facet joint replacement device, comprising:
    a housing defining a first opening, a second opening, and an internal space;
    a first rod having a longitudinal axis and a circular cross-sectional shape, the first rod slidingly engaged with the first opening, the first rod including an internal end portion disposed within the internal space and an external end portion disposed outside of the internal space;
    a second rod having a longitudinal axis and a circular cross-sectional shape, the second rod slidingly engaged with the second opening, the second rod including an internal end portion disposed within the internal space and an external end portion disposed outside of the internal space; and
    an elastic element disposed within the internal space, the elastic element coupled to and extending between the internal end portion of the first rod and the internal end portion of the second rod such that the first rod is spaced apart from the second rod by a spacing distance, wherein a longitudinal cross-sectional shape of the internal space taken along the longitudinal axes is elliptical.

11. The facet joint replacement device of claim 10, wherein the first rod and the second rod can be compressed toward each other such that the elastic element compresses and the spacing distance decreases.

12. The facet joint replacement device of claim 11, wherein the first rod and the second rod can be pulled away from each other such that the elastic element extends and the spacing distance increases.

13. The facet joint replacement device of claim 10, wherein the elastic element is a spring.

14. The facet joint replacement device of claim 10, wherein the first rod can be rotated around its longitudinal axis in relation to the second rod.

15. The facet joint replacement device of claim 10, wherein the housing is a molded component.

16. The facet joint replacement device of claim 10, wherein the first and second rods can rotate relative to the housing.

17. The facet joint replacement device of claim 10, wherein the first and second rods are restrained from rotating relative to the housing.

18. The facet joint replacement device of claim 10, wherein the elastic element is a polymeric element.

\* \* \* \* \*